(12) United States Patent
Kaij et al.

(10) Patent No.: US 12,365,914 B2
(45) Date of Patent: Jul. 22, 2025

(54) DISEASE RESISTANT SQUASH PLANTS

(71) Applicant: Enza Zaden Beheer B.V., Enkhuizen (NL)

(72) Inventors: Bart Kaij, Enkhuizen (NL); Yusuf Sen, Enkhuizen (NL); Quy Dung Dinh, Enkhuizen (NL)

(73) Assignee: Enza Zaden Beheer B.V., Enkhuizen (NL)

( * ) Notice: Subject to any disclaimer, the term of this patent is extended or adjusted under 35 U.S.C. 154(b) by 170 days.

(21) Appl. No.: 18/023,815

(22) PCT Filed: Sep. 1, 2020

(86) PCT No.: PCT/EP2020/074313
§ 371 (c)(1),
(2) Date: Feb. 28, 2023

(87) PCT Pub. No.: WO2022/048726
PCT Pub. Date: Mar. 10, 2022

(65) Prior Publication Data
US 2023/0279421 A1    Sep. 7, 2023

(51) Int. Cl.
  *C12N 15/82*  (2006.01)
  *A01H 5/08*   (2018.01)
  *A01H 6/34*   (2018.01)
  *C12N 9/12*   (2006.01)

(52) U.S. Cl.
  CPC ......... *C12N 15/8282* (2013.01); *A01H 5/08* (2013.01); *A01H 6/348* (2018.05); *C12N 9/1205* (2013.01); *C12Y 207/01039* (2013.01)

(58) Field of Classification Search
None
See application file for complete search history.

(56) References Cited

U.S. PATENT DOCUMENTS 8,237,019 B2    8/2012    Van Den Ackerveken et al.

FOREIGN PATENT DOCUMENTS

WO    2007051626 A2    5/2007

OTHER PUBLICATIONS

Perchepied et al., Relationship Between Loci Conferring Downy Mildew and Powdery Mildew Resistance in Melon Assessed by Quantitative Trait Loci Mapping, 2005, Phytopathology, vol. 95, pp. 556-565 (Year: 2005).*
Van Damme et al., Downy Mildew Resistance in *Arabidopsis* by Mutation of Homoserine Kinase, 2009, The Plant Cell, vol. 21, pp. 2179-2189 (Year: 2009).*
Van Damme et al., Downy Mildew Resistance in *Arabidopsis* by Mutation of Homoserine Kinase, 2009, The Plant Cell, vol. 21(7), pp. 2179-2189 (Year: 2009).*
Porterfield et al., Candidate Susceptibility Genes for Powdery and Downy Mildew in Watermelon and Squash, 2017, Journal of Phylogenetics & Evolutionary Biology, vol. 5(2), pp. 1-15 (Year: 2017).*
Van Den Ackerveken et al., 2013, U.S. Pat. No. 8,575,432 (Year: 2013).*
Brewer et al., "Mutations in the *Arabidopsis* homoserine kinase gene DMR1 confer enhanced resistance to Fusarium Culmorum and F. graminearum", BMC Plant Biology, 2014, pp. 1-15, vol. 14:317.
Holdsworth et al., "Cultivar-Based Introgression Mapping Reveals Wild Species-Derived Pm-0 , the Major Powdery Mildew Resistance Locus in Squash", PLOS One, Dec. 2016, pp. 1-20.
"Homoserine kinase [Cucurbita pepo subsp. pepo]", Database NCBI, pp. 1-2, received from https://www.nclainlnn.nih.gov/protein/XP_023554521, [Accessed May 11, 2021].
Huibers et al., "Powdery Mildew Resistance in Tomato by Impairment of SlPMR4 and SlDMR1", PLOS One, Jun. 2013, pp. 1-8, vol. 8:6.
Rehrig et al., "CaDMR1 Cosegregates with QTL Pc5.1 for Resistance to Phytophthora Capsici in Pepper (*Capsicum annuum*)", The Plant Genome, Jul. 2014, pp. 1-12, vol. 7:2.

* cited by examiner

Primary Examiner — Bratislav Stankovic
Assistant Examiner — Christina L Meadows
(74) Attorney, Agent, or Firm — The Webb Law Firm

(57) ABSTRACT

The present disclosure relates to squash plants that are resistant to the plant disease downy mildew caused by the pathogen *Pseudoperonospora cubensis* and/or powdery mildew caused by the pathogen *Erysiphe cichoracearum*. Specifically, the present disclosure relates to squash plants that are resistant to mildew disease including a mutated homoserine kinase gene encoding a mutated homoserine kinase protein. The present disclosure further relates to seeds, tissues, cells, or plant parts of the present squash plants, and to methods for identifying mildew resistant squash plants.

19 Claims, 6 Drawing Sheets
Specification includes a Sequence Listing.

FIG. 3

>protein sequence homoserine kinase Cucurbita pepo (SEQ ID No. 1)
MAMISFQPPLKSFAVPQVPSYNPKSVAVCCSLSLPSRTVVTAVEPAPVFASVKAFAPATVA
NLGPGFDFLGCAVDGLGDFVSLSVDSNVRPGEVAIANITGNDPNKLSKNPLYNCAGIAAIE
VMKMLGIRSVGLSLSLEKGLPLGSGLGSSAASAAAAAIAVNGLFGGKLGVEDLVLAGLKS
EEKVSGYHADNVAPAIMGGFILIRNYEPLELIRLKFPVEKELFFVLVSPEFEAPTKKMRAAL
PAEVGMPHHVWNCSQAGALVAAVLQGDVIGLGKALSSDKIVEPTRVPLIPGMGGVKKAA
IAAGAFGCTISGAGPTAVAVTDNKERGKEIGESMVMAFMREGNLKAVASVKRLDRVGAR
LIGSTPIDRV*

>coding sequence homoserine kinase Cucurbita pepo (SEQ ID No. 2)
ATGGCGATGATCTCTTTTCAGCCTCCATTAAAGTCGTTTGCGGTTCCTCAAGTTCCTTC
ATATAACCCTAAATCTGTCGCCGTCTGTTGCAGTTTGTCTCTTCCATCCAGAACCGTCG
TTACTGCCGTTGAACCTGCACCAGTCTTCGCCTCTGTGAAGGCATTCGCTCCGGCAACC
GTCGCTAATTTAGGCCCTGGCTTTGATTTCCTTGGCTGCGCCGTTGATGGCTTGGGCGA
TTTCGTCTCTCTCAGCGTTGATTCCAATGTTCGTCCAGGTGAGGTCGCAATCGCTAATA
TTACAGGCAATGACCCTAATAAACTCAGTAAAAACCCTCTGTATAATTGCGCTGGCAT
CGCCGCCATTGAGGTTATGAAAATGCTAGGGATTCGATCTGTCGGTCTTTCTCTTTCGC
TTGAGAAAGGTCTACCGCTGGGGAGTGGATTGGGATCGAGCGCAGCGAGTGCCGCTG
CTGCGGCGATTGCTGTTAATGGATTGTTCGGCGGAAAATTAGGAGTCGAGGATTTGGT
TCTCGCAGGGCTGAAATCGGAAGAGAAAGTTTCTGGATACCATGCGGACAATGTCGC
ACCTGCGATTATGGGCGGTTTCATTCTGATCCGGAATTACGAACCCTTGGAATTGATCC
GCCTGAAATTCCCGGTTGAGAAGGAGCTGTTCTTCGTATTGGTAAGCCCGGAATTCGA
AGCTCCAACGAAGAAAATGCGTGCTGCCCTGCCAGCTGAAGTTGGGATGCCGCACCAT
GTGTGGAATTGCAGCCAAGCAGGGGCGTTGGTAGCGGCTGTGCTGCAGGGAGACGTG
ATAGGATTGGGCAAAGCGTTGTCCTCCGACAAAATTGTAGAGCCAACGAGGGTTCCGT
TGATTCCAGGGATGGGTGGGGTCAAGAAGGCAGCCATTGCAGCCGGGGCATTCGGAT
GCACCATTAGTGGAGCAGGGCCGACGGCGGTGGCAGTGACGGACAACAAGGAGAGG
GGGAAGGAGATCGGGGAAAGTATGGTTATGGCGTTTATGAGGGAAGGGAATCTGAAA
GCTGTGGCATCTGTAAAGAGACTGGATCGAGTTGGTGCAAGGCTCATCGGATCCACTC
CCATAGACAGAGTTTAA

FIG. 4

>protein sequence homoserine kinase Cucurbita pepo comprising the A303T mutation (SEQ ID No. 3)

MAMISFQPPLKSFAVPQVPSYNPKSVAVCCSLSLPSRTVVTAVEPAPVFASVKAFAPATVA
NLGPGFDFLGCAVDGLGDFVSLSVDSNVRPGEVAIANITGNDPNKLSKNPLYNCAGIAAIE
VMKMLGIRSVGLSLSLEKGLPLGSGLGSSAASAAAAAIAVNGLFGGKLGVEDLVLAGLKS
EEKVSGYHADNVAPAIMGGFILIRNYEPLELIRLKFPVEKELFFVLVSPEFEAPTKKMRAAL
PAEVGMPHHVWNCSQAGALVAAVLQGDVIGLGKALSSDKIVEPTRVPLIPGMGGVKKAT
IAAGAFGCTISGAGPTAVAVTDNKERGKEIGESMVMAFMREGNLKAVASVKRLDRVGAR
LIGSTPIDRV*

>coding sequence homoserine kinase Cucurbita pepo comprising the G907A mutation (SEQ ID No. 4)

ATGGCGATGATCTCTTTTCAGCCTCCATTAAAGTCGTTTGCGGTTCCTCAAGTTCCTTC
ATATAACCCTAAATCTGTCGCCGTCTGTTGCAGTTTGTCTCTTCCATCCAGAACCGTCG
TTACTGCCGTTGAACCTGCACCAGTCTTCGCCTCTGTGAAGGCATTCGCTCCGGCAACC
GTCGCTAATTTAGGCCCTGGCTTTGATTTCCTTGGCTGCGCCGTTGATGGCTTGGGCGA
TTTCGTCTCTCTCAGCGTTGATTCCAATGTTCGTCCAGGTGAGGTCGCAATCGCTAATA
TTACAGGCAATGACCCTAATAAACTCAGTAAAAACCCTCTGTATAATTGCGCTGGCAT
CGCCGCCATTGAGGTTATGAAAATGCTAGGGATTCGATCTGTCGGTCTTTCTCTTTCGC
TTGAGAAAGGTCTACCGCTGGGGAGTGGATTGGGATCGAGCGCAGCGAGTGCCGCTG
CTGCGGCGATTGCTGTTAATGGATTGTTCGGCGGAAAATTAGGAGTCGAGGATTTGGT
TCTCGCAGGGCTGAAATCGGAAGAGAAAGTTTCTGGATACCATGCGGACAATGTCGC
ACCTGCGATTATGGGCGGTTTCATTCTGATCCGGAATTACGAACCCTTGGAATTGATCC
GCCTGAAATTCCCGGTTGAGAAGGAGCTGTTCTTCGTATTGGTAAGCCCGGAATTCGA
AGCTCCAACGAAGAAAATGCGTGCTGCCCTGCCAGCTGAAGTTGGGATGCCGCACCAT
GTGTGGAATTGCAGCCAAGCAGGGGCGTTGGTAGCGGCTGTGCTGCAGGGAGACGTG
ATAGGATTGGGCAAAGCGTTGTCCTCCGACAAAATTGTAGAGCCAACGAGGGTTCCGT
TGATTCCAGGGATGGGTGGGGTCAAGAAGGCAACCATTGCAGCCGGGGCATTCGGAT
GCACCATTAGTGGAGCAGGGCCGACGGCGGTGGCAGTGACGGACAACAAGGAGAGG
GGGAAGGAGATCGGGGAAAGTATGGTTATGGCGTTTATGAGGGAAGGGAATCTGAAA
GCTGTGGCATCTGTAAAGAGACTGGATCGAGTTGGTGCAAGGCTCATCGGATCCACTC
CCATAGACAGAGTTTAA

*  *           *
        Cucurbita pepo        MAMISFQPPLKSFAVPQVPSYNPKSVAVCCSLSLPSRTVVTAVEPAPVFASVKAFAPATV
  Cucurbita pepo mutant       MAMISFQPPLKSFAVPQVPSYNPKSVAVCCSLSLPSRTVVTAVEPAPVFASVKAFAPATV
      Cucurbita maxima        MAMISFQPPLKSFAVPLVPLYNPKSVAVSCSLSLPSRTVVTAVEPAPVFASVKAFAPATV
    Cucurbita moschata        MAMISFQPPLKSFAVPQVPLYNPKSVAVCCSLSLPSRTVVTAVEPAPVFASVKAFAPATV

*
        Cucurbita pepo        ANLGPGFDFLGCAVDGLGDFVSLSVDSNVRPGEVAIANITGNDPNKLSKNPLYNCAGIAA
  Cucurbita pepo mutant       ANLGPGFDFLGCAVDGLGDFVSLSVDSNVRPGEVAIANITGNDPNKLSKNPLYNCAGIAA
      Cucurbita maxima        ANLGPGFDFLGCAVDGLGDFVSLSVDSNVRPGEVAITNITGNDPNKLSKNPLYNCAGIAA
    Cucurbita moschata        ANLGPGFDFLGCAVDGLGDFVSLSVDSNVRPGEVAITNITGNDPNKLSKNPLYNCAGIAA

*
        Cucurbita pepo        IEVMKMLGIRSVGLSLSLEKGLPLGSGLGSSAASAAAAAIAVNGLFGGKLGVEDLVLAGL
  Cucurbita pepo mutant       IEVMKMLGIRSVGLSLSLEKGLPLGSGLGSSAASAAAAAIAVNGLFGGKLGVEDLVLAGL
      Cucurbita maxima        IEVMKMLGIRSVGLSLTLEKGLPLGSGLGSSAASAAAAAIAVNGLFGGKLGVEDLVLAGL
    Cucurbita moschata        IEVMKMLGIRSVGLSLSLEKGLPLGSGLGSSAASAAAAAIAVNGLFGGKLGVEDLVLAGL

*
        Cucurbita pepo        KSEEKVSGYHADNVAPAIMGGFILIRNYEPLELIRLKFPVEKELFFVLVSPEFEAPTKKM
  Cucurbita pepo mutant       KSEEKVSGYHADNVAPAIMGGFILIRNYEPLELIRLKFPVEKELFFVLVSPEFEAPTKKM
      Cucurbita maxima        KSEEKVSGYHADNVAPAIMGGFILIRNYEPLELIRLRFPVEKELFFVLVSPEFEAPTKKM
    Cucurbita moschata        KSEEKVSGYHADNVAPAIMGGFILIRNYEPLELIRLKFPVEKELFFVLVSPEFEAPTKKM Cucurbita pepo        RAALPAEVGMPHHVWNCSQAGALVAAVLQGDVIGLGKALSSDKIVEPTRVPLIPGMGGVK
  Cucurbita pepo mutant       RAALPAEVGMPHHVWNCSQAGALVAAVLQGDVIGLGKALSSDKIVEPTRVPLIPGMGGVK
      Cucurbita maxima        RAALPAEVGMPHHVWNCSQAGALVAAVLQGDVIGLGKALSSDKIVEPTRVPLIPGMGGVK
    Cucurbita moschata        RAALPAEVGMPHHVWNCSQAGALVAAVLQGDVIGLGKALSSDKIVEPTRVPLIPGMGGVK

*
        Cucurbita pepo        KAAIAAGAFGCTISGAGPTAVAVTDNKERGKEIGESMVAFMREGNLKAVASVKRLDRVG
  Cucurbita pepo mutant       KATIAAGAFGCTISGAGPTAVAVTDNKERGKEIGESMVAFMREGNLKAVASVKRLDRVG
      Cucurbita maxima        KAAIAAGAFGCTISGAGPTAVAVTDNKERGKEIGESMVAFMREGNLKAVASVKRLDRVG
    Cucurbita moschata        KAAIAAGAFGCTISGAGPTAVAVTDNKERGKEIGESMVAFMREGNLKAVASVKRLDRVG Cucurbita pepo        ARLIGSTPIDRV
  Cucurbita pepo mutant       ARLIGSTPIDRV
      Cucurbita maxima        ARLIGSTPIDRV
    Cucurbita moschata        ARLIGSTPIDRV
```

DISEASE RESISTANT SQUASH PLANTS

CROSS-REFERENCE TO RELATED APPLICATION

This application is the United States national phase of International Application No. PCT/EP2020/074313 filed Sep. 1, 2020, the disclosure of which is hereby incorporated by reference in its entirety.

The Sequence Listing associated with this application is filed in electronic format and is hereby incorporated by reference into the specification in its entirety. The name of the text file containing the Sequence Listing is 2300645_ST25.txt. The size of the text file is 9,826 bytes and the text file was created on Jan. 31, 2023.

BACKGROUND OF THE INVENTION

Field of the Invention

The present disclosure relates to squash plants that are resistant to the plant disease downy mildew and/or powdery mildew and especially relates to squash plants that are resistant to the downy mildew disease causing pathogen *Pseudoperonospora cubensis* and/or the powdery mildew disease causing pathogen *Erysiphe cichoracearum*. The present disclosure further relates to seeds, cells, tissues, or plant parts of the present squash plants and to methods for identifying mildew resistant squash plants.

Description of Related Art

Plants employ diverse constitutive and inducible defence strategies to counteract colonization by microbial pathogens and attacks of herbivorous insects. Plant responses induced upon pathogen encounter are triggered by non-self-recognition of common microbial structures and by highly pathogen specific effectors.

Obligate biotrophic phytopathogens such as the causal pathogens of powdery mildew and downy mildew employ highly specialized infection strategies. Genetic studies on *Arabidopsis* have identified several downy mildew resistance genes that appear to be involved in susceptibility to downy mildew oomycete pathogens. In *Arabidopsis*, knockdown mutations of these genes have been shown to provide protection against downy mildew. Map-based cloning revealed that a downy mildew resistance gene designated as DMR1 encodes a homoserine kinase (HSK) protein which catalyzes the conversion of homoserine to homoserine-4-phosphate, a step in the Aspartic acid (Asp)-derived Threonine (Thr) biosynthesis pathway. Mutating DMR1 causes the HSK protein substrate homoserine, which is present at low levels in the wild-type, to accumulate. The accumulation of homoserine is therefore one way to identify DMR1 mutant plants.

Because the DMR1 protein is important for the biosynthesis of essential amino acids, DMR1-based resistance (in which DMR1 is mutated) directly interferes with the biosynthesis of essential amino acids and overall plant vigour. This has made the development of viable and commercially interesting plants difficult. For example, if DMR1 expression is completely abolished (e.g., through introduction of a premature stop-codon in the coding sequence of DMR1), the resulting mutant plants have severely affected development or are unable to develop (i.e., the DMR1 mutation is lethal). Furthermore fruit set, ripening and fruit development may be affected, resulting in reduced fruit yield, quality and brix levels.

Accordingly, using DMR1-based resistance in plants requires a delicate balance between maintaining a sufficiently high concentration, or activity, of HSK protein in a plant cell to allow for adequate synthesis of essential amino acids and maintaining a sufficiently low concentration, or activity, of HSK protein in a plant cell to provide downy mildew resistance.

The genus *Cucurbita* includes the squash species. Pumpkins and courgette (zucchini) are types of squashes. Squashed have a great diversity of fruit forms and colours, from flattened, oblong or elongated, from white, yellow or green. Fruit surfaces may be smooth, ridged, or warty. The fruits develop rapidly and are often harvested within a few days after they form.

*Pseudoperonospora cubensis* is an oomycete plant pathogen that is known for causing downy mildew on cucurbits such as squash. *Pseudoperonospora cubensis* is an obligate biotroph that causes brown- to black-colored chlorotic lesions on the foliage. During humid conditions, inspection of the underside of the leaf reveals gray-brown to purplish-black fungal growth. Eventually, leaves of infected plants turn necrotic and curl upwards.

Once the pathogen has been detected in an area, management is essential, as *Pseudoperonospora cubensis* is nearly impossible to eradicate. Between long-surviving resting spores and high levels of secondary inoculum, *Pseudoperonospora cubensis* can affect many of the present squash plants in the field.

In addition, Powdery mildew is one of the main fungal diseases known in squash plants, both in the field and greenhouse. Powdery mildew diseases in squash are caused by the fungus *Erysiphe cichoracearum* (former *Golovinomyces cichoracearum*). The disease is characterized by distinctive symptoms such as white powder-like spots on the leaves and stems. Generally, the lower leaves are the most affected, but the mildew can appear on any part of the plant that is exposed above ground. As the disease progresses, the spots get larger and thicker as massive numbers of spores form, and the mildew spreads up and down the length of the plant such on the stem and even the fruits. Severely affected leaves can become dry and brittle or can wither and die. Because of the infection, the fruits can be smaller in size, fewer in number, less able to be successfully stored, sun scalded, incompletely ripe, and having a poor flavour. It may also predispose plants to be more vulnerable to other pathogens. Eventually, the plant can die.

Although many biological control products have been evaluated for their ability to control mildew infections (both downy and powdery mildew), none have proven effective, and so they are not recommended for use. Chemical control is effective and recommended because downy and powdery mildew are aggressive and destructive diseases and satisfactory control without the use of fungicides is unlikely. Such products need to be applied often to prevent pathogen resistance, and combinations or rotations with fungicides of a different mode of action are used to avoid pathogen resistance. However, some strains of *Erysiphe cichoracearum* show resistance to fungicides.

Considering the above, there is a need in the art for squash plants in which downy and/or powdery mildew resistance is encoded by a genetic determinant or resistance gene. It is an object of the present disclosure, amongst other objects, to address this need in the art.

SUMMARY OF THE INVENTION

This object of the present disclosure, amongst other objects, is met by the provision of a squash plant as outlined in the appended claims.

Specifically, this object of the present disclosure, amongst other objects, is met by a downy mildew resistant squash plant, wherein said squash plant comprises in its genome a homoserine kinase gene expressing a mutated homoserine kinase protein, wherein the mutation of the homoserine kinase protein comprises an amino acid substitution of the amino acid alanine (A) to the amino acid threonine (T) at position 303 of an homoserine kinase protein of which the amino acid sequence is shown in SEQ ID No. 1. SEQ ID No. 1 represents the wild type homoserine kinase protein sequence, not having the mutation, and SEQ ID No. 2 represents its coding sequence. The amino acid sequence of the homoserine kinase protein comprising the A303T mutation is shown in SEQ ID No. 3 and its coding sequence in SEQ ID No. 4.

The present inventors have surprisingly found that through amino acid substitution or a reduced, but not absent, expression, a sufficient activity of homoserine kinase (HSK) can be maintained in squash plants to allow for synthesis of essential amino acids and, simultaneously, a sufficient low activity of homoserine kinase (HSK) can be obtained to provide downy mildew resistance.

The mutation A303T in the wild type protein sequence of HSK (SEQ ID No. 1) can be provided by generally known plant mutagenesis techniques such as ethyl methane sulfonate (EMS), CRISPR-Cas, radiation, or by genetic modification of the HSK coding sequence as shown in SEQ ID No. 2.

According to another preferred embodiment, the present disclosure relates to the downy mildew resistant squash plant, wherein the squash plant is one or more selected from the group consisting of *Cucurbita pepo, Cucurbita maxima* and *Cucurbita moschata*, preferably *Cucurbita pepo*. All three *Cucurbita* species listed comprise a protein sequence of HSK having a sequence identity of at least 98% respectively to each other, as also indicated by their multiple alignment as show in FIG. 5.

According to another preferred embodiment, the present disclosure relates to the downy mildew resistant squash plant, wherein downy mildew is caused by the pathogen *Pseudoperonospora cubensis*.

According to a preferred embodiment, the present disclosure relates to the downy mildew resistant squash plant, wherein the plant is furthermore more tolerant to powdery mildew compared to a squash plant that does not comprise the mutated homoserine kinase protein.

According to another preferred embodiment, the present disclosure relates to the downy mildew resistant squash which is furthermore more tolerant to powdery mildew, wherein said powdery mildew is caused by the pathogen *Erysiphe cichoracearum*.

According to a preferred embodiment, the present disclosure relates to the downy mildew resistant squash plant, wherein said homoserine kinase gene is homozygously present in the genome of said squash plant. Experiments show that the mutation in the homoserine kinase has a recessive effect and therefore is preferably homozygous in the genome to affect homoserine accumulation and downy mildew resistance in squash.

According to another preferred embodiment, the present disclosure relates to the downy mildew resistant squash plant, wherein said squash plant comprises in its genome a homoserine kinase gene expressing a homoserine kinase protein of which the amino acid sequence is shown in SEQ ID No. 3.

According to yet another preferred embodiment, the present disclosure relates to the downy mildew resistant squash plant, wherein said squash plant comprises in its genome a homoserine kinase gene encoding a mutated cDNA, wherein the mutation of the cDNA comprises a nucleotide change of guanine to adenine at position 907 in the cDNA sequence of SEQ ID No. 2.

According to a preferred embodiment, the present disclosure relates to the downy mildew resistant squash plant, wherein said squash plant comprises in its genome a homoserine kinase gene encoding the cDNA sequence of SEQ ID No. 4.

According to another preferred embodiment, the present disclosure relates to downy mildew resistant squash plant, wherein the mutation of the homoserine kinase protein provides an in planta homoserine concentration of 25 to 200 ng/mg fresh weight, preferably 35 to 100 ng/mg fresh weight in the leaves of said plant. As indicated above, DMR1 (HSK) based resistance requires a delicate balancing between maintaining a sufficiently high concentration, or activity, of homoserine kinase (HSK) protein in a plant cell to allow for synthesis of essential amino acids and a sufficiently low concentration, or activity, of HSK protein in a plant cell to provide downy mildew resistance.

The present inventors have surprisingly found that in planta homoserine concentrations of at least 25 ng/mg fresh weight in the leaves, through amino acid substitution A303T in the HSK protein sequence, provides the present downy mildew resistance. It is noted that in susceptible plants homoserine concentrations are considerably lower than 25 ng/mg fresh weight, i.e. the homoserine levels in the susceptible plants tested did not exceed 1.0 ng/mg fresh weight.

According to yet another preferred embodiment, the present disclosure relates to the downy mildew resistant squash plant, wherein the mutation of the homoserine kinase protein provides an in planta homoserine concentration of 30 to 170 ng/mg fresh in the leaves, preferably 40 to 140 ng/mg, more preferably 45 to 125 ng/mg.

Considering the benefits of the squash plant as outlined above, the present disclosure also relates to seed, cell, fruit or plant part of the squash plant of present disclosure, wherein said seed, cell or plant part comprises in its genome a homoserine kinase gene capable of expressing a mutated homoserine kinase protein, wherein the mutation of the homoserine kinase protein comprises an amino acid substitution of the amino acid alanine (A) to the amino acid threonine (T) at position 303 of an homoserine kinase protein of which the amino acid sequence is shown in SEQ ID No. 1. The squash fruit obtained from a squash plant according to present disclosure, i.e. comprising the mutation in the DMR1 gene, was of good quality and suitable for commercial use.

According to another more preferred embodiment, the present disclosure relates to a mutated homoserine kinase protein, wherein the mutation comprises an amino acid substitution of the amino acid alanine (A) to the amino acid threonine (T) at position 303 of a homoserine kinase protein of which the amino acid sequence is shown in SEQ ID No. 1. The mutated homoserine kinase protein sequence is shown in SEQ ID No. 3.

According to a further aspect, the present disclosure relates to a cDNA capable of being translated into the mutated homoserine kinase of present disclosure or to a homoserine kinase gene capable of expressing the mutated homoserine kinase protein or of being transcribed into the cDNA.

According to a further aspect, the present disclosure relates to methods for identifying a mildew resistant squash, said method comprises the step of establishing the presence of the mutated homoserine kinase protein, the cDNA or the gene of present disclosure in said squash plant. The method of present invention can identify downy mildew resistant and/or powdery mildew tolerant squash plants.

According to a preferred embodiment, the present disclosure relates to the method, wherein said method comprises the step of establishing the presence of SEQ ID No. 3 or SEQ ID No. 4 in the squash plant.

According to a further aspect, the present disclosure relates to the use of the homoserine kinase gene of present disclosure, or the cDNA sequence thereof, for providing squash plants being resistant or having an increased resistance to the plant pathogen that causes mildew. Preferably the plant has increased resistance and/or tolerance against the pathogen that causes downy mildew and/or powdery mildew Certain aspects of the present disclosure relate to an isolated *Pseudoperonospora cubensis* resistant squash plant, wherein the squash plant includes amino acid sequence SEQ ID NO: 3. In some embodiments, the squash plant includes a gene encoding a protein having amino acid sequence SEQ ID NO: 3. In some embodiments, the gene is homozygously present in the genome of the squash plant. In some embodiments that may be combined with any of the preceding embodiments, the squash plant includes nucleotide sequence SEQ ID NO: 4. In some embodiments that may be combined with any of the preceding embodiments, the squash plant includes a gene with a coding sequence of nucleotide sequence SEQ ID NO: 4. In some embodiments, the gene is homozygously present in the genome of the squash plant.

In another aspect, the present disclosure provides an isolated *Pseudoperonospora cubensis* resistant squash plant, wherein the squash plant includes a mutated homoserine kinase gene encoding a mutated homoserine kinase protein, and wherein the mutation of the homoserine kinase protein includes an Alanine (A) to Threonine (T) amino acid substitution at a position corresponding to amino acid 303 of reference sequence SEQ ID NO: 1. In some embodiments, the mutated homoserine kinase gene has a mutated coding sequence wherein the mutation replaces a Guanine (G) with an Adenine (A) at a position corresponding to nucleotide 907 of reference sequence SEQ ID NO: 2. In some embodiments, the mutated coding sequence is homozygously present.

In some embodiments that may be combined with any of the preceding embodiments, the in planta homoserine concentration is about 25 to about 200 ng/mg fresh weight in leaves of the plant. In some embodiments that may be combined with any of the preceding embodiments, the in planta homoserine concentration is about 30 to 170 ng/mg, about 40 to 140 ng/mg, about 45 to 125 ng/mg fresh weight in leaves of the plant. In some embodiments that may be combined with any of the preceding embodiments, the in planta homoserine concentration is the result of the presence of SEQ ID NO: 3, the presence of SEQ ID NO: 4, the mutated homoserine kinase protein, the mutated coding sequence, or a combination thereof.

In some embodiments that may be combined with any of the preceding embodiments, the present disclosure provides a seed, cell, tissue, or plant part of an isolated squash plant including amino acid sequence SEQ ID NO: 3. In some embodiments, the seed, cell, tissue, or plant part includes a gene encoding a protein having amino acid sequence SEQ ID NO: 3. In some embodiments, the gene is homozygously present in the genome of the seed, cell, tissue, or plant part of the squash plant. In some embodiments that may be combined with any of the preceding embodiments, the seed, cell, tissue, or plant part of the squash plant includes nucleotide sequence SEQ ID NO: 4. In some embodiments that may be combined with any of the preceding embodiments, the seed, cell, tissue, or plant part of the squash plant includes a gene with a coding sequence of nucleotide sequence SEQ ID NO: 4. In some embodiments, the gene is homozygously present in the genome of the squash plant. In some embodiments that may be combined with any of the preceding embodiments, the present disclosure provides a seed, cell, tissue, or plant part of an isolated squash plant including a mutated homoserine kinase gene encoding a mutated homoserine kinase protein, wherein the mutation of the homoserine kinase protein includes an Alanine (A) to Threonine (T) amino acid substitution at a position corresponding to amino acid 303 of reference sequence SEQ ID NO: 1. In some embodiments, the mutated homoserine kinase gene has a mutated coding sequence wherein the mutation replaces a Guanine (G) with an Adenine (A) at a position corresponding to nucleotide 907 of reference sequence SEQ ID NO: 2. In some embodiments, the mutated coding sequence is homozygously present.

In an additional aspect, the present disclosure provides a method for identifying a *Pseudoperonospora cubensis* resistant squash plant including: establishing the presence of nucleotide sequence SEQ ID NO: 4 or establishing the presence of amino acid sequence SEQ ID NO: 3. In another aspect, the present disclosure provides a method for identifying a *Pseudoperonospora cubensis* resistant squash plant including: establishing the presence of a homoserine kinase coding sequence having nucleotide sequence SEQ ID NO: 4 or establishing the presence of a homoserine kinase protein having amino acid sequence SEQ ID NO: 3.

In yet another aspect, the present disclosure provides a method for obtaining a *Pseudoperonospora cubensis* resistant squash plant, including: mutating an amino acid sequence, wherein the mutation of the amino acid includes an Alanine (A) to Threonine (T) amino acid substitution at a position corresponding to amino acid 303 of reference sequence SEQ ID NO: 1. In still another aspect, the present disclosure provides a method for obtaining a *Pseudoperonospora cubensis* resistant squash plant, including: mutating a homoserine kinase protein, wherein the mutation of the homoserine kinase protein includes an Alanine (A) to Threonine (T) amino acid substitution at a position corresponding to amino acid 303 of reference sequence SEQ ID NO: 1. In some embodiments that may be combined with any of the preceding embodiments, the mutated amino acid sequence or mutated homoserine kinase protein has amino acid sequence SEQ ID NO: 3.

In a further aspect, the present disclosure provides a method for obtaining a *Pseudoperonospora cubensis* resistant squash plant, including: mutating a nucleotide sequence, wherein the mutation of the nucleotide sequence replaces a Guanine (G) with an Adenine (A) at a position corresponding to nucleotide 907 of reference sequence SEQ ID NO: 2. In another aspect, the present disclosure provides a method for obtaining a *Pseudoperonospora cubensis* resistant squash plant, including: mutating a homoserine kinase coding sequence, wherein the mutation of the coding sequence replaces a Guanine (G) with an Adenine (A) at a position corresponding to nucleotide 907 of reference sequence SEQ ID NO: 2. In some embodiments that may be combined with any of the preceding embodiments, the mutated nucleotide sequence or mutated coding sequence has nucleotide sequence SEQ ID NO: 4.

Yet another aspect of the present disclosure relates to a *Pseudoperonospora cubensis* resistant squash plant produced by any one of the preceding methods. In some embodiments, the squash plant includes amino acid sequence SEQ ID NO: 3. In some embodiments that may be combined with any of the preceding embodiments, the squash plant includes nucleotide sequence SEQ ID NO: 4. In some embodiments that may be combined with any of the preceding embodiments, the in planta homoserine concentration is about 25 to about 200 ng/mg fresh weight in leaves of the plant. In some embodiments that may be combined with any of the preceding embodiments, the in planta homoserine concentration is about 30 to 170 ng/mg, about 40 to 140 ng/mg, about 45 to 125 ng/mg fresh weight in leaves of the plant. In some embodiments that may be combined with any of the preceding embodiments, the in planta homoserine concentration is the result of the presence of SEQ ID NO: 3, the presence of SEQ ID NO: 4, the mutated homoserine kinase protein, the mutated coding sequence, or any combination thereof. Still another aspect of the present disclosure relates to a seed, cell, tissue, or plant part of the *Pseudoperonospora cubensis* resistant squash plant of any of the preceding embodiments.

BRIEF DESCRIPTION OF THE DRAWINGS

FIG. 2A shows wild type squash plants, which have brown-colored chlorotic lesions on the foliage. FIG. 2B shows A303T mutant squash plants, which have healthy foliage and are unaffected by the pathogen.

FIG. 3 shows the protein sequence (SEQ ID No. 1) of the wild type HSK of squash. SEQ ID No. 2 shows the cDNA sequence encoding the wild type HSK.

FIG. 4 shows the A303T mutant protein sequence (SEQ ID No. 3) of HSK of squash. SEQ ID No. 4 shows the cDNA sequence encoding the mutant HSK.

FIG. 5 shows the multiple alignment of the HSK protein of *Cucurbita pepo*, *Cucurbita maxima* and *Cucurbita moschata*, and the mutated HSK protein of *Cucurbita pepo* comprising the A303T mutation. The * indicates when an amino acid differs amongst the HSK protein of the *Cucurbita* species. All *Cucurbita* species listed comprise a protein sequence of HSK having a sequence identity of at least 98% respectively to each other, as also indicated by their highly identical multiple alignment.

FIG. 6A shows wild type squash plants, which have white sporulation on the foliage and plants show to be necrotic. FIG. 6B shows A303T mutant squash plants, which have healthy foliage that is largely unaffected by the pathogen and only the stems of the plant are slightly affected by the pathogen. The A303T mutant squash plants is more tolerant to powdery mildew infection that the wildtype plant.

DESCRIPTION OF THE INVENTION

Homoserine Kinase (HSK) Genes and Proteins

Figure 1:
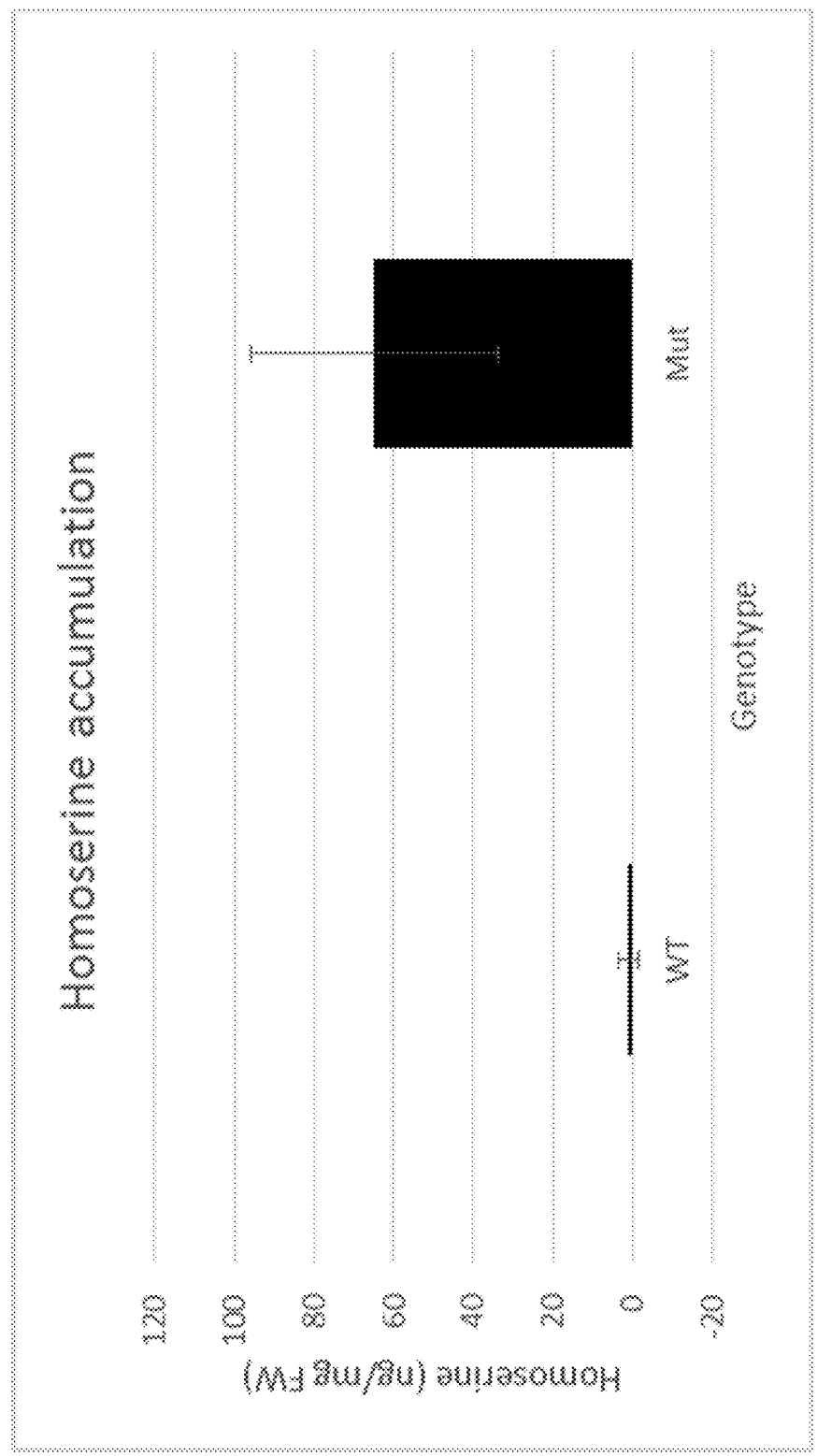
FIG. 1 shows the homoserine concentration in ng/mg fresh weight (FW) of wild type squash plant (*Cucurbita pepo*) and the A303T mutant squash plants (*Cucurbita pepo*). Wild type (wt) plants that have a wild type HSK protein do not accumulate homoserine. A303T mutant plants accumulates levels of homoserine of on average about 55-65 ng/mg FW.

The present disclosure generally relates to plants having a mutant homoserine kinase (HSK) gene. In some embodiments, a single nucleotide substitution in the coding sequence of the HSK gene results in downy mildew (e.g., *Pseudoperonospora cubensis*) resistance.

In some aspects, plants of the present disclosure relate to the downy mildew resistant squash plant, wherein the plant is furthermore more tolerant to powdery mildew compared to a squash plant that does not comprise the mutated homoserine kinase protein.

In some aspects, plants of the present disclosure are Squash plants. Squash plants contain one HSK gene, also known as DMR1. In some aspects, plants of the present disclosure have a mutation in the coding sequence of the HSK gene.

The nucleotide coding sequence of HSK is set forth in SEQ ID NO: 2. Provided herein are also homologs and orthologs of HSK. In some embodiments, a homolog or ortholog of HSK has a nucleic acid coding sequence that is at least 85%, at least 90%, at least 91%, at least 92%, at least 93%, at least 94%, at least 95%, at least 96%, at least 97%, at least 98%, or at least 99% identical to SEQ ID NO: 2. In some embodiments, a nucleic acid sequence encoding a homolog or ortholog of HSK may also have a mutation.

In some aspects, plants of the present disclosure have a mutation in the coding sequence of the HSK gene that replaces a Guanine (G) with an Adenine (A) at a position corresponding to nucleotide 907 of SEQ ID NO: 2 (i.e., a G907A mutation). In some aspects, plants of the present disclosure have a G907A mutant HSK coding sequence set forth in SEQ ID NO: 4.

In some aspects, plants of the present disclosure have a mutation in the amino acid sequence of the HSK protein. In some embodiments, the mutation is the result of the mutation in the coding sequence of the HSK gene.

The protein sequence of HSK is set forth in SEQ ID NO: 1. Provided herein are also homologs and orthologs of HSK. In some embodiments, a homolog or ortholog of HSK has an amino acid coding sequence that is at least 85%, at least 90%, at least 91%, at least 92%, at least 93%, at least 94%, at least 95%, at least 96%, at least 97%, at least 98%, or at least 99% identical to SEQ ID NO: 1. In some embodiments, an amino acid sequence encoding a homolog or ortholog of HSK may also have a mutation.

In some aspects, plants of the present disclosure have a mutation in the amino acid sequence of the HSK protein that replaces an Alanine (A) with a Threonine (T) at a position corresponding to amino acid 303 of SEQ ID NO: 1 (i.e., an A303T mutation). In some aspects, plants of the present disclosure have an A303T mutant HSK protein set forth in SEQ ID NO: 3.

In some aspects, the mutation may be a point mutation, a substitution mutation, wherein the mutation alters the coding sequence of the HSK gene and/or HSK polypeptide. In some aspects, the mutation may be a point mutation, a substitution mutation, wherein the mutation reduces the expression or activity of the HSK gene and/or HSK polypeptide.

A modified nucleic acid of the present disclosure (e.g., a mutated HSK gene) in a plant cell may have its expression or activity reduced by at least about 5%, at least about 10%, at least about 15%, at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% as compared to a corresponding control. Various controls will be readily apparent to one of skill in the art. For example, a control may be a corresponding plant or plant cell that does not contain a mutated nucleic acid encoding a mutated HSK polypeptide of the present disclosure.

A modified polypeptide of the present disclosure (e.g., a modified HSK polypeptide having reduced expression or activity) in a plant cell may have its expression or activity reduced by at least about 5%, at least about 10%, at least about 15%, at least about 20%, at least about 25%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% as compared to a corresponding control. Various controls will be readily apparent to one of skill in the art. For example, a control may be a corresponding plant or plant cell that does not contain a modified HSK polypeptide of the present disclosure.

Homoserine Concentration

The present disclosure generally relates to plants having an in planta homoserine concentration of about 25 to about 200 ng/mg fresh weight in the leaves of the plant. It was surprisingly found that in planta homoserine concentrations of at least 25 ng/mg fresh weight in the leaves provided downy mildew (e.g., *Pseudoperonospora cubensis*) resistance. It was further found that in susceptible plants, homoserine concentrations were considerably lower than 25 ng/mg fresh weight in the leaves.

Plants of the present disclosure with an in planta homoserine concentration of about 25 to 5 about 200 ng/mg fresh weight in the leaves of the plant may have an in planta homoserine concentration of at least about 25 ng/mg, at least about 30 ng/mg, at least about 35 ng/mg, at least about 40 ng/mg, at least about 45 ng/mg, at least about 50 ng/mg, at least about 60 ng/mg, at least about 70 ng/mg, at least about 80 ng/mg fresh weight in the leaves of the plant.

Plants of the Present Disclosure

In some aspects, plants of the present disclosure are plants of the family *Cucurbitaceae* and of the genus *Cucumis*. In some embodiments, plants of the present disclosure are plants of the species squash. In some embodiments, plants of the present disclosure are squash plants, preferably selected from the group consisting of *Cucurbita pepo, Cucurbita maxima* and *Cucurbita moschata*, preferably *Cucurbita pepo*. All three *Cucurbita* species listed comprise a protein sequence of HSK having a sequence identity of at least 98% respectively to each other, as also indicated by their multiple alignment as show in FIG. 5.

According to the present description plant parts include, but are not limited to, leaves, stems, meristems, cotyledons, hypocotyl, roots, root tips, root meristems, ovules, pollen, anthers, pistils, flowers, embryos, seeds, fruits, parts of fruits, cells, and the like. Plant tissues may be tissues or any plant part. Plant cells may be cells of any plant part. The squash fruit obtained from a squash plant according to present disclosure, i.e. comprising the mutation in the DMR1 gene, was of good quality and suitable for commercial use.

Plants of the present disclosure include plants with increased in planta homoserine concentration as compared to a control plant (e.g., a plant of the same species that does not have a mutated HSK gene or protein, for example, a wild-type plant). In some embodiments, plants of the present disclosure have an in planta homoserine concentration of at least 25 ng/mg fresh weight in the leaves of the plant. In some embodiments, plants of the present disclosure have an in planta homoserine concentration of about 25 to about 200 ng/mg fresh weight in the leaves of the plant may have an in planta homoserine concentration of at least about 25 ng/mg, at least about 30 ng/mg, at least about 35 ng/mg, at least about 40 ng/mg, at least about 45 ng/mg, at least about 50 ng/mg, at least about 60 ng/mg, at least about 70 ng/mg, at least about 80 ng/mg. Plants can be tested for in planta homoserine concentrations using commonly known methods in the art.

Methods of Increasing Homoserine, Mutating HSK, and Obtaining Plants of the Present Disclosure The endogenous homoserine level can be increased by lowering the enzymatic activity of the homoserine kinase gene which leads to a lower conversion of homoserine (e.g., into downstream intermediates in the amino acid biosynthesis pathways) and as a result, homoserine accumulates. Alternatively, the expression of the homoserine kinase enzyme can be reduced. This also leads to a lower conversion of homoserine and results in homoserine accumulation. Reducing the expression of the homoserine kinase gene can in itself be achieved in various ways, either directly, such as by gene silencing, or indirectly by modifying the regulatory sequences thereof or by stimulating repression of the gene.

Modulating the HSK gene to lower its activity or expression can be achieved at various levels. In particular, to achieve a reduced HSK activity, the expression of the HSK gene can be down-regulated or the enzymatic activity of the HSK protein can be reduced by amino acid substitutions resulting from nucleotide changes in the HSK coding sequence.

In some embodiments, the endogenous HSK gene can be directly mutated. Alternatively, the expression of the HSK gene can be reduced at the regulatory level, for example by modifying the regulatory sequences or by gene silencing. In some embodiments, one or more regulators of the HSK gene are downregulated (in case of transcriptional activators) by RNA interference (RNAi), virus-induced gene silencing (VIGS), small RNA-mediated post-transcriptional gene silencing, transcription activator-like effector nuclease (TALEN) genome editing techniques, Clustered Regularly Interspaced Short Palindromic Repeat (CRISPR/Cas) genome editing techniques, and/or zinc-finger nuclease (ZFN) gene editing techniques. In other embodiments, regulators are upregulated (in case of repressor proteins) by transgenic overexpression. Overexpression is achieved in a particular embodiment by expressing repressor proteins of the HSK gene from a strong promoter, e.g. the 35S promoter that is commonly used in plant biotechnology. The down-regulation of the HSK gene can also be achieved by mutagenesis of the regulatory elements in the promoter, terminator region, or potential introns.

Mutations that affect expression of the HSK gene or activity of the HSK protein are induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in the HSK gene can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641), the individual plants that have a mutation in the gene of interest are identified. By screening many plants, a large collection of mutant alleles is obtained, each giving a different effect on gene expression or enzyme activity.

Mutations in the HSK gene can also be induced in plants by using a gene editing technique, which enables targeted mutation. In some embodiments, the gene editing technique is selected from the group of transcription activator-like effector nuclease (TALEN) gene editing techniques, clustered Regularly Interspaced Short Palindromic Repeat (CRISPR/Cas9) gene editing techniques, or zinc-finger nuclease (ZFN) gene editing techniques. In some embodiments, the mutation is introduced using one or more vectors including gene editing components selected from the group of a CRISPR/Cas9 system, a TALEN, a zinc finger, and a meganuclease designed to target a nucleic acid sequence encoding a HSK gene.

A modified HSK gene can be brought into the plant by means of transgenic techniques. Plant transformation involves the construction of an expression vector that will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid and can be used alone or in combination with other plasmids, to provide transformed squash plants. Promoters may be inducible, constitutive, tissue-specific or tissue-preferred. Methods for plant transformation include biological methods and physical methods (See, for example, Miki, et al., "Procedures for Introducing Foreign DNA into Plants" in *Methods in Plant Molecular Biology and Biotechnology*, Glick and Thompson Eds., CRC Press, Inc., Boca Raton, pp. 67-88 (1993)). In addition, expression vectors and in vitro culture methods for plant cell or tissue transformation and regeneration of plants are available (See, for example, Gruber, et al., "Vectors for Plant Transformation" in *Methods in Plant Molecular Biology and Biotechnology*, Glick and Thompson Eds., CRC Press, Inc., Boca Raton, pp. 89-119 (1993)). The produced transgenic line could then be crossed, with another (non-transformed or transformed) line, in order to produce a new transgenic squash line. Alternatively, a genetic trait which has been engineered into a particular squash cultivar using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene.

A modified HSK gene can be brought into the plant by means of breeding. The breeding technique called backcrossing allows essentially all of the desired morphological and physiological characteristics of a cultivar to be recovered in addition to the single gene transferred into the line (e.g., the modified HSK gene). The parental squash plant which contributes the gene for the desired characteristic (e.g., the modified HSK gene) is termed the nonrecurrent or donor parent. This terminology refers to the fact that the nonrecurrent parent is used one time in the backcross protocol and therefore does not recur. The parental squash plant to which the gene or genes from the nonrecurrent parent are transferred is known as the recurrent parent as it is used for several rounds in the backcrossing protocol. In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a squash plant is obtained wherein essentially all of the desired morphological and physiological characteristics of the recurrent parent are recovered in the converted plant, in addition to the single transferred gene from the nonrecurrent parent. The present disclosure further relates to methods for developing squash plants in a squash plant breeding program using plant breeding techniques including recurrent selection, backcrossing, pedigree breeding, restriction fragment length polymorphism enhanced selection, and genetic marker enhanced selection.

Plants of the present disclosure can be identified by multiple methods. The gene expression or protein levels can for example be tested by analysis of HSK transcript levels (e.g. by RT-PCR). Another option is the quantification of HSK protein levels with antibodies, or amino acid analysis, measuring homoserine accumulation as a result of reduced HSK activity. The skilled person can also use the usual pathogen tests to see if the homoserine accumulation is sufficient to induce pathogen resistance. These methods are known to the person skilled in the art and can be used to identify plants of the present disclosure. Plants with the desired reduced HSK level or HSK expression are then propagated, back-crossed or crossed to other breeding lines to transfer only the desired new allele into the background of the crop wanted.

Examples

The following examples are provided to further illustrate aspects of the present disclosure. These examples are non-limiting and should not be construed as limiting any aspect of the present disclosure.

Example 1: Generation of HSK A303T Mutant Squash Plants

Seeds of squash (*Cucurbita pepo* homozygous parental line SL0166) were treated with the mutagenic agent Ethyl Methanesulfonate (EMS) in order to introduce random point mutations. The HSK (DMR1) gene located on chromosome 1 was the target gene for the introduction of random point mutations. In addition, samples were taken from the top of the developing shoots of the squash plants for further molecular analysis and mutant population screening, i.e., the detection of mutations in candidate genes as described by Van Eijk and Van Tunen in EP 1929039. Mutated plants were grown to produce seeds and the next generation was screened for increased accumulation of homoserine. This was achieved by measuring levels of the amino acid homoserine.

This process identified the A303T mutant, which was selected. The A303T mutation was an Alanine (A) to Threonine (T) amino acid substitution at a position corresponding to amino acid 303 of the HSK protein (WT HSK protein sequence=SEQ ID NO: 1; mutant A303T HSK protein sequence=SEQ ID NO: 3). Further, the HSK coding sequence was mutated in A303T mutant plants. Specifically, a Guanine (G) was replaced with an Adenine (A) at a position corresponding to nucleotide 907 in the HSK coding sequence (WT HSK coding sequence=SEQ ID NO: 2; mutant G907A HSK coding sequence=SEQ ID NO: 4).

The A303T mutant plants had high homoserine concentration in ng/mg fresh weight (FW) of plant leaves, see FIG. 1. Wild type (wt) plants that have a wild type HSK protein do not accumulate homoserine. A303T mutant plants accumulates levels of homoserine of on average about 55-65 ng/mg FW.

The A303T mutant plants were made homozygous by selfing or inter-crossing. The homozygous A303T mutant plants showed full resistance to downy mildew upon *Pseudoperonospora cubensis* infection (see Example 2).

Example 2: Downy Mildew (*Pseudoperonospora cubensis*) Infection Assay

Wild type and mutant A303T squash plants were exposed to downy mildew (*Pseudoperonospora cubensis*) infection in green house conditions. Infection with *P. cubensis* was done when the plants had 5-8 leaves. The disease scoring was done approximately 30 days post infection, and measurements were taken on in total 341 plants; 59 wild type (WT) plants, 192 A303T heterozygous (HE) plants, and 90 A303T homozygous (HO) plants. Table 1 provides a detailed description of the disease scoring scale used in the infection assay. Briefly, disease scoring was performed on the scale of 1 to 9, where a score of 1 indicated that plants were fully susceptible and showed necrosis while a score of 9 indicated that plants were fully resistant and showed no symptoms of infection.

TABLE 1

Downy mildew assay scoring scale

| Score | Lower surface of leaf phenotype | Upper surface of leaf phenotype |
|---|---|---|
| 1 | Heavy sporulation | Completely yellow with dry areas |
| 2 | Heavy sporulation | Angular yellow spots that cover more than 85% of the surface |
| 3 | Heavy sporulation | Angular yellow spots that cover more than 75% of the surface |
| 4 | Heavy sporulation | Angular yellow spots that cover more than 60% of the surface |
| 5 | Sporulation | Angular yellow spots that cover 50% of the surface |
| 6 | Slight sporulation | Angular yellow spots that cover 30% of the surface |
| 7 | No sporulation | Angular yellow spots that cover less than 10% of the surface |
| 8 | No symptoms | One spot or no symptoms |
| 9 | No symptoms | No symptoms |

Figure 2A:
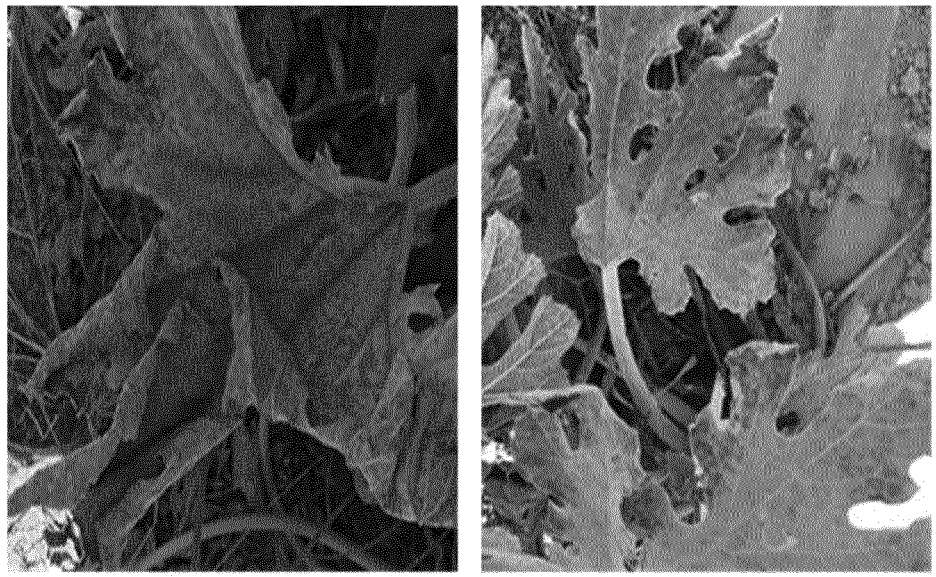
FIGS. 2A-2B show representative images of downy mildew (*Pseudoperonospora cubensis*) infection on wild type and A303T mutant squash plants (*Cucurbita pepo*).
Figure 2B:

The results of the downy mildew assay are shown in Table 2. The homozygous A303T plants were consistently resistant (score of about 8). In contrast, the heterozygous A303T plants were susceptible, and showed similar results to the WT plants. FIGS. 2A-2B show representative images of WT and homozygous A303T mutant plants during testing respectively. These results indicate that the A303T mutation is preferably present homozygously in order to provide downy mildew resistance.

TABLE 2

Downy mildew assay results

| Genotype | Downy mildew disease score, # of plants | | | | | | | |
|---|---|---|---|---|---|---|---|---|
| | 1 | 2 | 3 | 4 | 5 | 6 | 7 | 8 |
| A303T (HO) | 0 | 0 | 1 | 5 | 1 | 0 | 3 | 80 |
| A303T (HE) | 0 | 0 | 79 | 101 | 9 | 1 | 1 | 0 |
| WT | 0 | 0 | 21 | 34 | 2 | 0 | 2 | 0 |

Example 3: Powdery Mildew (*Erysiphe cichoracearum*) Infection Assay

Wild type and A303T mutant squash plants were exposed to powdery mildew (*Erysiphe cichoracearum*) infection. Infection was done on adult plants.

The first disease scoring was done approximately 45 days after infection on a wild type (WT) plants and mutant plants. A second disease scoring was done approximately 60 days post infection. Table 3 provides a detailed description of the disease scoring scale used in the powdery mildew infection assay. Briefly, disease scoring was performed on the scale of 1 to 9, where a score of 1 meant plants were fully susceptible and showed necrosis while a score of 9 meant plants were fully resistant and showed no symptoms of infection.

TABLE 3

Powdery mildew assay scoring scale

| Score | Lower surface of leaf phenotype | Upper surface of leaf phenotype |
|---|---|---|
| 1 | Heavy sporulation | Completely white sporulation with dry areas |
| 2 | Heavy sporulation | White sporulation that cover more than 90% of the surface |
| 3 | Heavy sporulation | White sporulation that cover more than 80% of the surface |
| 4 | Heavy sporulation | White sporulation that cover more than 60% of the surface |
| 5 | Sporulation | White sporulation that cover 40-50% of the surface |
| 6 | Slight sporulation | White sporulation that cover 20-30% of the surface |
| 7 | No sporulation | White sporulation that cover 10-20% of the surface |
| 8 | No symptoms | White sporulation that cove less than 10% of the surface |
| 9 | No symptoms | No symptoms |

Figure 6:
FIGS. 6A-6B show representative images of powdery mildew (*Erysiphe cichoracearum*) infection on wild type and A303T mutant squash plants (*Cucurbita pepo*) wherein disease scoring was done 45 days post infection.
Figure 6:

The results of the powdery mildew assay are shown in FIGS. 6A and 6B. The mutant A303T plants showed to be resistant (score of 9) on their leaves, and some degree of infection was observed on their stem (score of 6) at the first scoring around day 45 (FIG. 6B), whereas the wild type plants were fully susceptible for both leaves and stem (score of 1 to 3) (FIG. 6A). However, at the second scoring around day 60, the leaves were still mostly free of powdery mildew (score 8 to 9) but the stem of the mutant plants were fully infected (score of 1 to 3). The wild type plants at day 60 remained fully infected for both leaves and stem (score of 1 to 3). These results indicate that the A303T mutation in the DMR1 gene provides powdery mildew tolerance. The powdery mildew infection seems to be delayed in the mutant plants, but eventually the mutant plants also become infected.

SEQUENCE LISTING

```
<160> NUMBER OF SEQ ID NOS: 4

<210> SEQ ID NO 1
<211> LENGTH: 372
<212> TYPE: PRT
<213> ORGANISM: Cucurbita pepo

<400> SEQUENCE: 1

Met Ala Met Ile Ser Phe Gln Pro Pro Leu Lys Ser Phe Ala Val Pro
1               5                   10                  15

Gln Val Pro Ser Tyr Asn Pro Lys Ser Val Ala Val Cys Cys Ser Leu
            20                  25                  30

Ser Leu Pro Ser Arg Thr Val Val Thr Ala Val Glu Pro Ala Pro Val
        35                  40                  45

Phe Ala Ser Val Lys Ala Phe Ala Pro Ala Thr Val Ala Asn Leu Gly
    50                  55                  60

Pro Gly Phe Asp Phe Leu Gly Cys Ala Val Asp Gly Leu Gly Asp Phe
65                  70                  75                  80

Val Ser Leu Ser Val Asp Ser Asn Val Arg Pro Gly Glu Val Ala Ile
                85                  90                  95

Ala Asn Ile Thr Gly Asn Asp Pro Asn Lys Leu Ser Lys Asn Pro Leu
            100                 105                 110

Tyr Asn Cys Ala Gly Ile Ala Ala Ile Glu Val Met Lys Met Leu Gly
        115                 120                 125

Ile Arg Ser Val Gly Leu Ser Leu Ser Leu Glu Lys Gly Leu Pro Leu
    130                 135                 140

Gly Ser Gly Leu Gly Ser Ser Ala Ala Ser Ala Ala Ala Ala Ala Ile
145                 150                 155                 160

Ala Val Asn Gly Leu Phe Gly Gly Lys Leu Gly Val Glu Asp Leu Val
                165                 170                 175

Leu Ala Gly Leu Lys Ser Glu Glu Lys Val Ser Gly Tyr His Ala Asp
            180                 185                 190

Asn Val Ala Pro Ala Ile Met Gly Gly Phe Ile Leu Ile Arg Asn Tyr
        195                 200                 205

Glu Pro Leu Glu Leu Ile Arg Leu Lys Phe Pro Val Glu Lys Glu Leu
    210                 215                 220

Phe Phe Val Leu Val Ser Pro Glu Phe Glu Ala Pro Thr Lys Lys Met
225                 230                 235                 240

Arg Ala Ala Leu Pro Ala Glu Val Gly Met Pro His His Val Trp Asn
                245                 250                 255

Cys Ser Gln Ala Gly Ala Leu Val Ala Ala Val Leu Gln Gly Asp Val
            260                 265                 270

Ile Gly Leu Gly Lys Ala Leu Ser Asp Lys Ile Val Glu Pro Thr
        275                 280                 285

Arg Val Pro Leu Ile Pro Gly Met Gly Gly Val Lys Lys Ala Ala Ile
    290                 295                 300

Ala Ala Gly Ala Phe Gly Cys Thr Ile Ser Gly Ala Gly Pro Thr Ala
305                 310                 315                 320

Val Ala Val Thr Asp Asn Lys Glu Arg Gly Lys Glu Ile Gly Glu Ser
```

```
                        325                 330                 335
Met Val Met Ala Phe Met Arg Glu Gly Asn Leu Lys Ala Val Ala Ser
                340                 345                 350

Val Lys Arg Leu Asp Arg Val Gly Ala Arg Leu Ile Gly Ser Thr Pro
                355                 360                 365

Ile Asp Arg Val
        370

<210> SEQ ID NO 2
<211> LENGTH: 1119
<212> TYPE: DNA
<213> ORGANISM: Cucurbita pepo

<400> SEQUENCE: 2
atggcgatga tctctttca gcctccatta aagtcgtttg cggttcctca agttccttca      60 tataaccta aatctgtcgc cgtctgttgc agtttgtctc ttccatccag aaccgtcgtt    120
actgccgttg aacctgcacc agtcttcgcc tctgtgaagg cattcgctcc ggcaaccgtc    180
gctaatttag gccctggctt tgatttcctt ggctgcgccg ttgatggctt gggcgatttc    240
gtctctctca gcgttgattc caatgttcgt ccaggtgagg tcgcaatcgc taatattaca    300
ggcaatgacc ctaataaact cagtaaaaac cctctgtata attgcgctgg catcgccgcc    360
attgaggtta tgaaaatgct agggattcga tctgtcggtc tttctctttc gcttgagaaa    420
ggtctaccgc tggggagtgg attgggatcg agcgcagcga gtgccgctgc tgcggcgatt    480
gctgttaatg gattgttcgg cggaaaatta ggagtcgagg attggttct cgcagggctg    540 aaatcggaag agaaagtttc tggataccat gcggacaatg tcgcacctgc gattatgggc    600
ggtttcattc tgatccggaa ttacgaaccc ttggaattga tccgcctgaa attcccggtt    660
gagaaggagc tgttcttcgt attggtaagc ccggaattcg aagctccaac gaagaaaatg    720
cgtgctgccc tgccagctga agttgggatg ccgcaccatg tgtggaattg cagccaagca    780
ggggcgttgg tagcggctgt gctgcaggga gacgtgatag gattgggcaa agcgttgtcc    840
tccgacaaaa ttgtagagcc aacgagggtt ccgttgattc cagggatggg tggggtcaag    900
aaggcagcca ttgcagccgg gcattcggat gcaccatta gtggagcagg gccgacggcg    960
gtggcagtga cggacaacaa ggagaggggg aaggagatcg ggaaagtat ggttatggcg   1020 tttatgaggg aagggaatct gaaagctgtg gcatctgtaa agagactgga tcgagttggt   1080
gcaaggctca tcggatccac tcccatagac agagtttaa                        1119

<210> SEQ ID NO 3
<211> LENGTH: 372
<212> TYPE: PRT
<213> ORGANISM: Cucurbita pepo

<400> SEQUENCE: 3

Met Ala Met Ile Ser Phe Gln Pro Pro Leu Lys Ser Phe Ala Val Pro
1               5                   10                  15

Gln Val Pro Ser Tyr Asn Pro Lys Ser Val Ala Val Cys Cys Ser Leu
                20                  25                  30

Ser Leu Pro Ser Arg Thr Val Val Thr Ala Val Glu Pro Ala Pro Val
        35                  40                  45

Phe Ala Ser Val Lys Ala Phe Ala Pro Ala Thr Val Ala Asn Leu Gly
    50                  55                  60

Pro Gly Phe Asp Phe Leu Gly Cys Ala Val Asp Gly Leu Gly Asp Phe
65                  70                  75                  80
```

```
Val Ser Leu Ser Val Asp Ser Asn Val Arg Pro Gly Glu Val Ala Ile
                85                  90                  95
Ala Asn Ile Thr Gly Asn Asp Pro Asn Lys Leu Ser Lys Asn Pro Leu
            100                 105                 110
Tyr Asn Cys Ala Gly Ile Ala Ala Ile Glu Val Met Lys Met Leu Gly
        115                 120                 125
Ile Arg Ser Val Gly Leu Ser Leu Ser Leu Glu Lys Gly Leu Pro Leu
    130                 135                 140
Gly Ser Gly Leu Gly Ser Ser Ala Ala Ser Ala Ala Ala Ala Ala Ile
145                 150                 155                 160
Ala Val Asn Gly Leu Phe Gly Gly Lys Leu Gly Val Glu Asp Leu Val
                165                 170                 175
Leu Ala Gly Leu Lys Ser Glu Glu Lys Val Ser Gly Tyr His Ala Asp
            180                 185                 190
Asn Val Ala Pro Ala Ile Met Gly Gly Phe Ile Leu Ile Arg Asn Tyr
        195                 200                 205
Glu Pro Leu Glu Leu Ile Arg Leu Lys Phe Pro Val Glu Lys Glu Leu
    210                 215                 220
Phe Phe Val Leu Val Ser Pro Glu Phe Glu Ala Pro Thr Lys Lys Met
225                 230                 235                 240
Arg Ala Ala Leu Pro Ala Glu Val Gly Met Pro His His Val Trp Asn
                245                 250                 255
Cys Ser Gln Ala Gly Ala Leu Val Ala Ala Val Leu Gln Gly Asp Val
            260                 265                 270
Ile Gly Leu Gly Lys Ala Leu Ser Asp Lys Ile Val Glu Pro Thr
        275                 280                 285
Arg Val Pro Leu Ile Pro Gly Met Gly Gly Val Lys Lys Ala Thr Ile
    290                 295                 300
Ala Ala Gly Ala Phe Gly Cys Thr Ile Ser Gly Ala Gly Pro Thr Ala
305                 310                 315                 320
Val Ala Val Thr Asp Asn Lys Glu Arg Gly Lys Glu Ile Gly Glu Ser
                325                 330                 335
Met Val Met Ala Phe Met Arg Glu Gly Asn Leu Lys Ala Val Ala Ser
            340                 345                 350
Val Lys Arg Leu Asp Arg Val Gly Ala Arg Leu Ile Gly Ser Thr Pro
        355                 360                 365
Ile Asp Arg Val
        370

<210> SEQ ID NO 4
<211> LENGTH: 1119
<212> TYPE: DNA
<213> ORGANISM: Cucurbita pepo

<400> SEQUENCE: 4
atggcgatga tctcttttca gcctccatta aagtcgtttg cggttcctca agttccttca      60 tataaccct aatctgtcgc cgtctgttgc agtttgtctc ttccatccag aaccgtcgtt      120
actgccgttg aacctgcacc agtcttcgcc tctgtgaagg cattcgctcc ggcaaccgtc      180
gctaatttag gccctggctt tgatttcctt ggctgcgccg ttgatggctt gggcgatttc      240
gtctctctca gcgttgattc caatgttcgt ccaggtgagg tcgcaatcgc taatattaca      300
ggcaatgacc ctaataaact cagtaaaaac cctctgtata attgcgctgg catcgccgcc      360
attgaggtta tgaaaatgct agggattcga tctgtcggtc tttctctttc gcttgagaaa      420
```

```
ggtctaccgc tggggagtgg attgggatcg agcgcagcga gtgccgctgc tgcggcgatt      480
gctgttaatg gattgttcgg cggaaaatta ggagtcgagg atttggttct cgcagggctg      540
aaatcggaag agaaagtttc tggataccat gcggacaatg tcgcacctgc gattatgggc      600
ggtttcattc tgatccggaa ttacgaaccc ttggaattga tccgcctgaa attcccggtt      660
gagaaggagc tgttcttcgt attggtaagc ccggaattcg aagctccaac gaagaaaatg      720
cgtgctgccc tgccagctga agttgggatg ccgcaccatg tgtggaattg cagccaagca      780
ggggcgttgg tagcggctgt gctgcaggga gacgtgatag gattgggcaa agcgttgtcc      840
tccgacaaaa ttgtagagcc aacgagggtt ccgttgattc cagggatggg tggggtcaag      900
aaggcaacca ttgcagccgg ggcattcgga tgcaccatta gtggagcagg gccgacggcg      960
gtggcagtga cggacaacaa ggagaggggg aaggagatcg gggaaagtat ggttatggcg     1020
tttatgaggg aagggaatct gaaagctgtg gcatctgtaa agagactgga tcgagttggt     1080
gcaaggctca tcggatccac tcccatagac agagtttaa                            1119
```

The invention claimed is:

1. A downy mildew resistant squash plant, wherein said squash plant comprises in its genome a homoserine kinase gene expressing a mutated homoserine kinase protein, wherein the mutation of the homoserine kinase protein comprises an amino acid substitution of the amino acid alanine (A) to the amino acid threonine (T) at position 303 of a homoserine kinase protein of which the amino acid sequence is shown in SEQ ID No. 1.

2. The downy mildew resistant squash plant according to claim 1, wherein said squash plant is one or more selected from the group consisting of Cucurbita pepo, Cucurbita maxima and Cucurbita moschata.

3. The downy mildew resistant squash plant according to claim 1, wherein downy mildew is caused by the pathogen Pseudoperonospora cubensis.

4. The downy mildew resistant squash plant according to claim 1, wherein said plant is furthermore more tolerant to powdery mildew compared to a squash plant that does not comprise the mutated homoserine kinase protein.

5. The downy mildew resistant squash plant according to claim 4, wherein said powdery mildew is caused by the pathogen Erysiphe cichoracearum.

6. The downy mildew resistant squash plant according to claim 1, wherein said homoserine kinase gene is homozygously present in the genome of said squash plant.

7. The downy mildew resistant squash plant according to claim 1, wherein said squash plant comprises in its genome a homoserine kinase gene expressing a homoserine kinase protein of which the amino acid sequence is shown in SEQ ID No. 3.

8. The downy mildew resistant squash plant according to claim 1, wherein said squash plant comprises in its genome a homoserine kinase gene encoding a mutated cDNA, wherein the mutation of the cDNA comprises a nucleotide change of guanine to adenine at position 907 in the cDNA sequence of SEQ ID No. 2.

9. The downy mildew resistant squash plant according to claim 1, wherein said squash plant comprises in its genome a homoserine kinase gene encoding the cDNA sequence of SEQ ID No. 4.

10. The downy mildew resistant squash plant according to claim 1, wherein the mutation of the homoserine kinase protein provides an in planta homoserine concentration of 25 to about 200 ng/mg fresh weight in leaves of the plant.

11. A seed, cell, or plant part of a squash plant according to claim 1, wherein said seed, cell, or plant part comprises in its genome a homoserine kinase gene capable of expressing a mutated homoserine kinase protein, wherein the mutation of the homoserine kinase protein comprises an amino acid substitution of the amino acid alanine (A) to the amino acid threonine (T) at position 303 of a homoserine kinase protein of which the amino acid sequence is shown in SEQ ID No. 1.

12. A mutated homoserine kinase protein, wherein the mutation comprises an amino acid substitution of the amino acid alanine (A) to the amino acid threonine (T) at position 303 of a homoserine kinase protein of which the amino acid sequence is shown in SEQ ID No. 1.

13. The mutated homoserine kinase protein according to claim 12 of which the amino acid sequence is shown in SEQ ID No. 3.

14. A cDNA capable of being translated into the mutated homoserine kinase protein of claim 12.

15. A homoserine kinase gene capable of expressing the mutated homoserine kinase protein of claim 12.

16. A method for identifying a mildew resistant squash plant, said method comprises the step of establishing the presence of the mutated homoserine kinase protein of claim 12 in said squash plant.

17. The method according to claim 16, wherein said method comprises the step of establishing the presence of SEQ ID No. 3 or SEQ ID No. 4 in said squash plant.

18. A method of producing a squash plant that is resistant to a plant pathogen that causes downy mildew, the method comprising introducing the homoserine kinase gene of claim 15 into the genome of a squash plant that is susceptible to the plant pathogen that causes downy mildew.

19. A method of producing a squash plant that is resistant to a plant pathogen that causes downy mildew, the method comprising introducing a mutation into a homoserine kinase gene that encodes a protein having the sequence of SEQ ID NO: 1 in a plant that is susceptible to the plant pathogen that causes downy mildew, the mutation resulting in an A303T substitution in SEQ ID NO: 1.

* * * * *